United States Patent [19]

Arakawa et al.

[11] 4,048,147
[45] Sept. 13, 1977

[54] CARBOXYLIC ACID OF CYCLOPENTADIENE DERIVATIVE, SALT THEREOF, OR ESTER THEREOF AND PROCESS FOR PRODUCING THESE COMPOSITIONS

[75] Inventors: Masatoshi Arakawa; Ryotaro Ohno; Katuhiro Ishikawa; Noboru Yamahara; Hisashi Matsui, all of Yokkaichi, Japan

[73] Assignee: Japan Synthetic Rubber Co., Ltd., Tokyo, Japan

[21] Appl. No.: 635,630

[22] Filed: Nov. 26, 1975

[30] Foreign Application Priority Data

Nov. 30, 1974 Japan .................. 49-136642

[51] Int. Cl.$^2$ .................. C08G 2/00; C08G 2/18; C08G 10/00

[52] U.S. Cl. .................. 260/67 UA; 162/168 R; 162/168 N; 260/29.7 R; 260/78.3 UA; 260/473 F; 526/11.1; 526/94; 526/201; 526/202; 526/340; 560/1; 560/57; 560/59

[58] Field of Search ....... 260/67 A, 67 UA, 78.3 UA; 526/11.1

[56] References Cited

U.S. PATENT DOCUMENTS

| | | | |
|---|---|---|---|
| 2,494,758 | 1/1950 | Hartough et al. | 260/67 A |
| 3,437,634 | 4/1969 | Veuse | 260/67 A |
| 3,448,082 | 6/1969 | McGraft et al. | 260/67 A |
| 3,898,201 | 8/1975 | Ishibe et al. | 526/11.1 |
| 3,957,736 | 5/1976 | Tsuchiya et al. | 526/11.1 |

Primary Examiner—Herbert J. Lilling
Attorney, Agent, or Firm—Oblon, Fisher, Spivak, McClelland & Maier

[57] ABSTRACT

A novel compound represented by the formula,

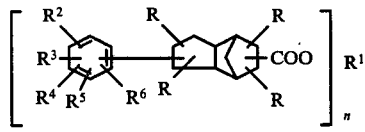

wherein R is a hydrogen or an alkyl group having 1 to 3 carbon atoms, said four R's being the same or different; $R^1$ is hydrogen, an alkali metal, an ammonium group, a mono-to tetra-hydric aliphatic alcohol moiety having 1 to 12 carbon atoms, or an organic amine residue; $n$ is an integer of 1 to 4; and $R^2$, $R^3$, $R^4$, $R^5$ and $R^6$ are independently hydrogen or alkyl groups having 1 to 6 carbon atoms or $R^2$ and $R^3$ may form a ring when taken together. Said novel compound has properties similar to those of natural rosin or a disproportionated rosin, and is useful as a vehicle for coating compositions and printing inks, as an emulsifier for emulsion polymerization, and as a sizing agent.

34 Claims, No Drawings

CARBOXYLIC ACID OF CYCLOPENTADIENE DERIVATIVE, SALT THEREOF, OR ESTER THEREOF AND PROCESS FOR PRODUCING THESE COMPOSITIONS

This invention relates to a resin containing in its molecule a cyclopentadiene skeleton, a benzene nucleus, and a carboxyl group and to a process for producing said resin. More particularly, it relates to a resin comparable in performance characteristics to natural rosin and to a process for producing said resin.

Natural rosin and its derivatives have been widely used in various fields. For example, an alkali salt of the natural rosin has an excellent anionic surface activity and is used as an emulsifier in the production of a styrene-butadiene rubber (SBR) or an acrylonitrile-butadiene-styrene resin (ABS resin) by emulsion polymerization. An SBR or an ABS resin produced by use of these emulsifiers acquires more favorable performance characteristcs owing to a tackifying effect of the natural rosin.

Further, polyol esters of the natural rosin are widely used as a hot-melt adhesive and a tackifier for adhesive tape, and exhibit superior properties to those of conventional synthetic resins, owing to their appropriate softening point, solubility in many solvents, and compatibility with many polymeric substances.

In paper industry, a paper which is not blurred even when written with a water-color ink is obtained by use of an alkali salt of natural rosin as either an internal size or a surface size. The sizing effect of a natural rosin is far superior to that of conventional petroleum resins. Natural rosin is widely used also in paints, printing inks, flooring, and road paving.

As mentioned above, natural rosin and its derivatives have been utilized in many fields, exhibiting excellent properties in each use field, and established a firm position not replaceable by conventional synthetic resins such as terpene and other petroleum resins. Being a natural product, however, rosin is in limited supply and, in recent years, its price has ever been increased. Moreover, the quality of natural rosin varies depending on the area where it was collected and the method whereby it was processed. Consequently, the advent of a synthetic resin comparable in properties to the natural rosin has been eagerly desired. Under the circumstances, the present inventors conducted extensive studies on the manufacture of a synthetic resin which may take the place of natural rosin, and as a result, it has been found that a specific derivative of cyclopentadiene is equivalent in properties to natural rosin.

An object of this invention is to provide a novel resin having a cyclopentadiene skeleton, benzene nucleus, and carboxyl group.

Another object of this invention is to provide a novel resin comparable in performance characteristics to natural rosin.

A further object of this invention is to provide an emulsifier containing said novel resin as major component.

Other objects and advantages of this invention will become apparent from the following description.

According to this invention, there is provided a carboxylic acid of cyclopentadiene derivative, a salt thereof, or an ester thereof having the formula,

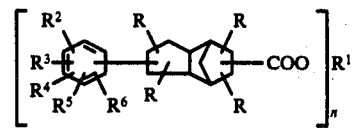

wherein R is hydrogen or an alkyl group having 1 to 3 carbon atoms, said four R's being either the same or different; $R^1$ is hydrogen, a mono- to tetra-hydric aliphatic alcohol moiety having 1 to 12 carbon atoms, preferably 1 to 6 carbon atoms, an alkali or alkaline earth metal, an ammonium group, or an organic amine residue; $n$ is an integer of 1 to 4; and $R^2$, $R^3$, $R^4$, $R^5$ and $R^6$, which may be the same or different, are independently hydrogen atoms or alkyl groups having 1 to 6 carbon atoms, or $R^2$ and $R^3$ may form a ring when taken together.

The carboxylic acid of cyclopentadiene derivatives, salt thereof, or ester thereof defined above is manufactured in the following ways:

1. The above-defined carboxylic acid or a salt thereof is produced by reacting a carboxylic ester of a dimer of at least one member of the group consisting of cyclopentadiene and alkylcyclopentadienes (hereinafter this group of cyclopentadiene and alkylcyclopentadienes is collectively referred to as cyclopentadienes) and/or a nitrile of said dimer with benzene and/or a benzene derivative represented by the formula,

wherein $R^2$, $R^3$, $R^4$, $R^5$ and $R^6$ have the same meanings as defined above in the presence of a Friedel-Crafts catalyst, and hydrolyzing the reaction product.

2. The above-defined carboxylic acid, a salt thereof, or an ester thereof, is produced by reacting an aldehyde of a dimer of at least one member of the cyclopentadienes with benzene and/or the above-mentioned benzene derivative in the presence of a Friedel-Crafts catalyst, oxidizing the reaction product, and, if necessary, neutralizing or esterifying the oxidation product.

3. The above-defined carboxylic ester of a cyclopentadiene derivative is produced by reacting a carboxylic ester of a dimer of at least one member of cyclopentadienes with benzene and/or the above-mentioned benzene derivative in the presence of a Friedel-Crafts catalyst, or esterifying the present carboxylic acid with a mono- to tetra-hydric aliphatic alcohol or subjecting the present ester to transesterification.

The cyclopentadienes for use in the present invention include cyclopentadiene and alkylcyclopentadienes such as methylcyclopentadiene, ethylcyclopentadiene, propylcyclopentadiene, and the like. In view of availability and economy, cyclopentadiene is most suitable.

The dimers of at least one member of cyclopentadienes include dicyclopentadiene, co-dimers of cyclopentadiene and an alkylcyclopentadiene, homodimers of the same alkylcyclopentadiene and co-dimers of different alkylcyclopentadienes. Of these, dicyclopentadiene is most suitable for use in view of availability and economy. Dicyclopentadiene is easily obtained by dimerization of cyclopentadiene contained in the $C_5$-fraction from naphtha cracking. In this dimerization reaction, there are formed as by-products co-dimers of cyclopentadiene and an open chain conjugated diene such as isoprene. Even when these co-dimers contain a compound having a norbornene ring, they may be used to accomplish the object of this invention.

For the sake of brevity, an explanation of the invention is made below by referring to dicyclopentadiene as a representative of the dimers of at least one member of cyclopentadienes.

The carboxylic ester of dicyclopentadiene used in this invention may be prepared by any known method without particular restriction. Since the decomposition temperature of dicyclopentadiene is, however, about 140° C, there should be avoided any method in which the reaction temperature is higher than said decomposition temperature.

Of the two double bonds in the dicyclopentadiene molecule, which is represented by the formula given below, the double bond in the norbornene ring is generally more reactive. Accordingly, esterification takes place preferentially at the double bond in the norbornene ring.

Examples of the suitable methods for esterification are given below, and they are by way of illustration and not by way of limitation.

1. Dicyclopentadiene, nickel carbonyl, Ni(CO)$_4$, and an alcohol are reacted at the reflux temperature of nickel carbonyl.

2. Dicyclopentadiene and an alcohol are reacted in carbon monoxide under pressure by using a metal carbonyl, metal complex, or metal salt of nickel, cobalt, rhodium, palladium, or platinum as catalyst.

3. Dicyclopentadiene, hydrogen, and carbon monoxide are reacted under pressure in the presence of a cobalt-containing catalyst such as cobalt carbonyl or a cobalt salt, rhodium-containing catalyst, iron-containing catalyst or the like, to effect hydroformylation, oxidizing the reaction product to obtain a carboxylic acid, and reacting the carboxylic acid with an alcohol in a customary way to yield an ester.

4. Dicyclopentadiene, water, and carbon monoxide are reacted under pressure in the presence of a cobalt catalyst such as cobalt carbonyl or a cobalt salt, iron-containing catalyst, iridium-containing catalyst, palladium-containing catalyst, platinum-containing catalyst, or the like to effect carboxylation, and reacting the resulting carboxylic acid with an alcohol in a usual manner to obtain an ester.

Although not subject to any particular restriction, the alcohol component which forms the carboxylic ester of dicyclopentadiene is preferably a lower aliphatic monoalcohol having 1 to 6, most preferably 1 to 3, carbon atoms.

There is no restriction placed upon the method for producing a dicyclopentadiene nitrile. For example, a method in which dicyclopentadiene and hydrogen cyanide are reacted by use of palladium or cobalt carbonyl as catalyst can be used with favorable results.

There is also no restriction placed upon the method for manufacturing a dicyclopentadiene aldehyde. It is conveniently produced, for example, by a method for hydroformylating dicyclopentadiene with hydrogen and carbon monoxide under pressure by using a cobalt catalyst such as cobalt carbonyl or a cobalt salt.

The addition reaction of a carboxylic ester, nitrile, or aldehyde of dicyclopentadiene to benzene and/or the above-mentioned benzene derivative can be carried out by use of a known Friedel-Crafts catalyst such as a boron trifluoride compound, hydrogen fluoride, aluminum chloride, or sulfuric acid usually at a temperature of 0° to 100° C for a reaction time of 1 to 20 hours with stirring. The benzene derivatives to be used include mono-, di-, tri-, tetra- or penta-alkyl-substituted benzenes such as toluene, ethylbenzene, cumene, cymene, xylene, 1,2,4-trimethylbenzene, and the like and tetrahydronaphthalene. The alkyl group has preferably 1 to 6 carbon atoms.

The reaction product of a carboxylic ester and/or nitrile of dicyclopentadiene with benzene and/or the above-mentioned benzene derivative can be converted into a carboxylic acid or a salt thereof by hydrolysis with an acid such as hydrochloric acid, sulfuric acid, acetic acid, or aromatic sulfonic acid, or a base, e.g., alkali metal hydroxide, or alkaline earth metal hydroxide in an ordinary manner, such as at a temperature of 80° to 200° C (when the ester is used, 80° to 100° C are preferable). The reaction product of a dicyclopentadiene aldehyde with benzene and/or the above-mentioned benzene derivative can be converted into a carboxylic acid in a customary manner by oxidation with an oxidant, such as chromic acid; a permanganate, e.g. sodium or potassium permanganate; or silver oxide, at a temperature of 0° to 80° C, preferably 0° to 30° C, more preferably room temperature. The carboxylic acid thus obtained has the structure,

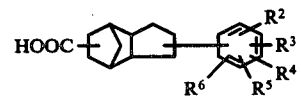

wherein $R^2$, $R^3$, $R^4$, $R^5$ and $R^6$ have the same meanings as defined above.

The present carboxylic acid can be esterified with a mono-to tetra-hydric aliphatic alcohol having 1 to 12 carbon atoms, preferably 1 to 6 carbon atoms, more preferably glycerin or pentaerythritol, at 50° to 100° C, preferably 70° to 100° C in the absence of a catalyst to obtain the desired ester. The ester may, if desired, be subjected to transesterification under similar conditions. The present carboxylic acid may be neutralized with an organic amine, e.g., hydroxylamine, methylamine, ethylamine, diethylamine, dimethylamine, trimethylamine or triethylamine.

The carboxylic acid of cyclopentadiene derivatives, the ester thereof, or the salt thereof according to this invention has the following properties and performance characteristics which resemble those of natural rosin.

1. It has bulky lyophilic and hydrophilic groups in the molecule.
2. The molecular weight is constant.
3. It is widely soluble in many solvents and widely compatible with many polymeric substances.
4. It has a relatively high softening point though has a low molecular weight.
5. It has a tackifying effect.

Because of the absence of a lone double bond or conjugated double bond, the present carboxylic acid of a cyclopentadiene derivative is superior in resistance to oxidation and chemicals to a natural rosin. The present carboxylic acid may be varied freely in HLB, softening point, and the acid value by varying the type of alkyl group in alkylcyclopentadienes and alkylbenzenes used as the starting materials.

As mentioned above, the present carboxylic acid of cyclopentadiene derivatives, salt thereof, or ester thereof has properties similar to those of natural rosin or a disproportionated rosin and, hence, has uses in common with these natural rosin products. For example, the present free acids can be used as tackifier, and the present esters are useful as vehicles for printing inks and surface coatings such as, paints, clear lacquer, varnish, traffic paint, etc.; and printing inks. An ester obtained by the reaction of the acid with a polyhydric alcohol having 3 to 5 carbon atoms is particularly suitable. Besides these esters, salts of the present carboxylic acid with polyvalent metals such as calcium, zinc, magnesium, etc. are also suitable as vehicles for printing inks, paints, such as traffic paint; adhesives, such as an adhesive for floor tile. The esters, particularly those obtained by the reaction with mono- to tetra-hydric alcohols having 1 to 12 carbon atoms, preferably 1 to 6 carbon atoms are used as tackifier in rubber compounding and as adhesive when compounded with thermoplastic synthetic resins. These esters are obtained by the reaction of the carboxylic acid of cyclopentadiene derivatives with various alcohols (mono- or poly-hydric alcohols). The reaction product of a carboxylic ester of the dimer with benzene and/or the above-mentioned benzene derivative can be used as such or after being subjected to transesterification.

Metal salts, particularly alkali metal salts, of the present carboxylic acid of cyclopentadiene derivatives are useful as sizing agents such as a paper size.

Above all, the present alkali metal salts of the carboxylic acids of cyclopentadiene derivatives are particularly useful as an emulsifier used in emulsion polymerization of synthetic rubbers such as SBR or synthetic resins such as ABS resins.

The invention is illustrated below in detail with reference to Examples which, however, are merely illustrative but not limitative. In Examples, all parts and percentages are by weight unless otherwise specified. The acid value and softening point therein were measured according to the following methods:

Acid value: JIS K 3341
Softening point: JIS K 2581 (ring and ball method)

EXAMPLE 1

[1] Preparation of ester of cyclopentadiene dimer

In a 1,000-ml flask provided with stirring blades were placed 300 ml of ethyl alcohol, 16.5 ml of acetic acid, 11 ml of water, and 150 g of cyclopentadiene dimer. After addition of 45 ml of nickel carbonyl, the mixture was allowed to react at 50° C for 2 hours. Thereafter, 100 ml of nickel carbonyl was further added and the reaction was allowed to continue at 50° C for another 2 hours. After completion of the reaction, the reaction mixture was admixed with 200 ml of 4N $H_2SO_4$ to decompose the nickel carbonyl, then extracted with petroleum ether, and distilled under reduced pressure to obtain 145 g of the intended ester having a boiling range from 80° to 100° C/2 mmHg.

[2] Preparation of carboxylic acid

In a 300-ml flask provided with stirring blades, which had been flashed with nitrogen to replace the air, were placed 100 g of toluene an 25 g of aluminum chloride. To the resulting solution maintained at 70° C was added dropwise with stirring 30 g of the ester obtained in [1] over a period of about 1 hour. After the end of dropwise addition, the mixture was kept at 70° C for a further 8 hours to continue the reaction. After the reaction had been complete, the reaction mixture was washed with a dilute aqueous solution of sodium hydroxide, freed from the precipitate by filtration, washed with water, and distilled to obtain 21g of a fraction boiling at 130° to 160° C/1.5 mmHg. This ester fraction was allowed to react with an equivalent or larger amount of an aqueous solution of potassium hydroxide at 80° C to yield an aqueous potassium carboxylate solution. The resulting solution was freed from the unsaponifiable matter by washing with ether, acidified with 10-% hydrochloric acid to obtain the intended carboxylic acid in the free state, which had an acid value of 205 and a softening point of 37.5° C.

EXAMPLE 2

[1] Preparation of nitrile of cyclopentadiene dimer

Into a 2-liter autoclave were charged 600 g of dicyclopentadiene, 270 g of hydrogen cyanide, 170 g of cobalt carbonyl [$Co_2(CO)_8$], and 85 g of triphenylphosphine. The resulting mixture was allowed to react with stirring at 130° C for 10 hours. After completion of the reaction, the gas was purged and the reaction mixture was diluted with 500 ml of benzene. The residual catalyst was removed from the diluted reaction mixture by filtration. The filtrate was transferred into a separating funnel, washed with a dilute aqueous solution of sodium hydroxide, dilute hydrochloric acid, and water in this order, and dried. On distillation of the resulting reaction product, 170 g of a nitrile boiling at 130° to 140° C/14 mmHg was obtained.

[2] Preparation of carboxylic acid

In a 300-ml flask provided with stirring blades, which had been flashed with nitrogen to replace the air, were placed 100 g of toluene and 25 g of aluminum chloride. To the resulting solution maintained at 70° C was added dropwise with stirring 30 g of the nitrile obtained in [1] over a period of about 1.5 hours. After the end of dropwise addition, the mixture was kept at 70° C for a further 8 hours to continue the reaction. After the reaction had been complete, the reaction mixture was washed with a dilute aqueous solution of sodium hydroxide, freed from the precipitate by filtration, washed with water, and dried. The resulting reaction product was allowed to react with an aqueous solution of potassium hydroxide in an autoclave at 200° C for 5 hours. After the removal of by-product ammonia, hydrochloric acid was added to obtain the carboxylic acid in the free state from the aqueous soap solution, and distilled to obtain a fraction boiling at 190° to 205° C/1 mmHg and having an acid value of 205 and a softening point of 37.5° C.

EXAMPLE 3

[1] Preparation of aldehyde of cyclopentadiene dimer

After the air in a 500-ml autoclave containing 50 g of dicyclopentadiene had been replaced by nitrogen, 100 ml of a benzene solution containing 3 % of cobalt carbonyl [$Co_2(CO)_8$] and a mixture (1 : 1 molar ratio) of carbon monoxide and hydrogen under a pressure of 150 kg/cm² were introduced into the autoclave. The temperature of the autoclave was elevated to 110° C, whereupon gas absorption took place and hydroformylation set in. When, of the two double bonds of dicyclopentadiene, only that in norbornene ring had been hydroformylated, as affirmed by gas chromatography, the reaction was terminated. After termination of the reaction, the residual gas was purged and the reaction mixture was diluted with 300 ml of n-hexane. The diluted reaction mixture was washed with 2N hydrochloric acid under an air stream until the red color of the oil layer disappeared. The resulting reaction mixture was washed with water, dried, and distilled to obtain 21 g of the aldehyde fraction boiling at 80° to 100° C/1 mmHg.

[2] Preparation of carboxylic acid

In a 300-ml flask provided with a stirrer, which had been flashed with nitrogen to replace the air, were placed 100 g of toluene and 25 g of aluminum chloride. To the resulting solution maintained at 70° C was added dropwise with stirring 30 g of the aldehyde obtained in [1] over a period of about one hour. After the end of dropwise addition, the mixture was kept at 70° C for further 8 hours to continue the reaction. After the reaction had been complete, the reaction mixture was washed with a dilute aqueous solution of sodium hydroxide, freed from the precipitate by filtration, washed with water, dried, and oxidized with potassium permanganate to obtain the intended carboxylic acid having an acid value of 205 and a softening point of 37.5° C.

EXAMPLE 4

In a 300-ml flask provided with a stirrer, after the air in which had been replaced by nitrogen, were placed 127 g of xylene and 25 g of aluminum chloride. To the resulting solution maintained at 70° C, was added with stirring 40 g of the ester obtained in [1] of Example 1 dropwise over a period of about 1 hour. After the end of dropwise addition, the mixture was kept at 70° C for a further 8 hours to continue the reaction. After the reaction has been complete, the reaction mixture was washed with a dilute aqueous solution of sodium hydroxide, separated from the precipitate by filtration, washed with water, dried, and distilled to obtain 22 g of a fraction boiling at 125° to 175° C/1 mmHg. This ester fraction was allowed to react with an equivalent or larger amount of an aqueous solution of potassium hydroxide at 80° C to yield an aqueous potassium carboxylate solution. The resulting solution was separated from the unsaponifiable matter by washing with ether, acidified with 10-% hydrochloric acid to set free the intended carboxylic acid having an acid value of 195 and a softening point of 38° C.

EXAMPLE 5

Table 1

| | Parts |
|---|---|
| Butadiene | 71 |
| Styrene | 29 |
| Water | 200 |
| Emulsifier | 4.5 |
| $Na_3PO_4 \cdot 12H_2O$ | 0.18 |
| Sodium dodecylbenzenesulfonate | 0.15 |
| $Fe_2SO_4 \cdot 7H_2O$ | 0.03 |
| Tetrasodium ethylenediaminetetraacetate | 0.05 |
| Sodium formaldehyde sulfoxylate | 0.08 |
| Tert-dodecylmercaptan | 0.18 |
| p-Menthane hydroperoxide | 0.08 |

Emulsion-copolymerization of styrene and butadiene was carried out at 5° C according to the formulation given in Table 1, using as the emulsifier a disproportionated rosin soap and soaps prepared by neutralizing the carboxylic acids obtained in Examples 1 to 4 with an aqueous solution of potassium hydroxide. The polymerization was terminated at a styrene-butadiene conversion of 60%. In each case, the stability of the emulsion during polymerization was satisfactory. The time required for 60 % conversion in each case was as shown in Table 2. The properties of the soaps obtained according to this invention were found to be better than those of a disproportionated rosin soap.

Table 2

| Run No. | 1 | 2 | 3 | 4 | 5 |
|---|---|---|---|---|---|
| Emulsifier | Disproportionated rosin acid soap | Example 1 | Example 2 | Example 3 | Example 4 |
| Time required for 60% conversion (min.) | 450 | 430 | 430 | 435 | 450 |

EXAMPLE 6

The same procedure as in Example 1 [2] was repeated, except that cumene or tert-butylbenzene containing 7 % by weight of sec-butylbenzene was substituted for the toluene to obtain the intended carboxylic acid in the free state. When cumene was used, the carboxylic acid obtained had an acid value of 146 and a boiling point of 195° to 210° C/1 mmHg, and when the tert-butyl-benzene was used, the carboxylic acid obtained had an acid value of 177 and a boiling point of 198° to 215° C/1 mmHg.

The above two acids were neutralized with an aqueous solution of potassium hydroxide to obtain potassium salts of the carboxylic acids. These potassium salts and commercially available rosin size and petroleum resin size were used as internal sizing agents to determine the sizing effects thereof in the following manner:

L-BKP having a degree of beating of 32°SR was added to water in a concentration 1% by weight. To the resulting pulp slurry was added each of the above sizing agents in a proportion of 1 % by weight (as solids) based on the weight of the pulp with stirring, and subsequently an aqueous aluminum sulfate solution was added thereto in a proportion of 3% by weight (as solids) based on the weight of the pulp. The resulting mixture was sufficiently stirred and the pH of the mixture was adjusted to 4.5. The thus obtained mixture was applied to a square type sheet machine in a basis weight of 60 g/m² to make a paper, which was dried at 80° C for 5 min. The thus obtained papers were subjected to measurement of sizing effect according to the Stockigt method of JIS-P-8122 to obtain the results shown in Table 3.

Table 3

| | Sizing agent | Sizing effect (sec) |
|---|---|---|
| Present invention | A[1] | 23 |
| | B[2] | 27 |
| Comparison | Rosin size[3] | 23 |
| | Petroleum resin size[4] | 22 |

Note:
[1] Sizing agent obtained by use of cumene.
[2] Sizing agent obtained by use of tert-butylbenzene.
[3] Rondis R (disproportionated rosin) made by Arakawa Rinsan Kogyo Kabushiki Kaisha.
[4] Size Petron 702 made by Arakawa Rinsan Kogyo Kabushiki Kaisha.

What is claimed is:
1. A composition represented by the formula,

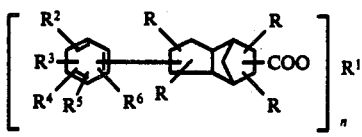

wherein R is hydrogen or an alkyl group having 1 to 3 carbon atoms, said four R groups being the same or different; $R^1$ is hydrogen, a mono- to tetra-hydric aliphatic alcohol moiety having 1 to 12 carbon atoms, an alkali or alkaline earth metal, an ammonium group, or an organic amine residue; $n$ is an integer of 1 to 4; and $R^2$, $R^3$, $R^4$, $R^5$ and $R^6$, which may be the same or different, are independently hydrogen or alkyl groups having 1 to 6 carbon atoms, or $R^2$ and $R^3$ may form a ring when taken together.

2. The composition according the claim 1, wherein all of said R groups are hydrogen 3. The composition according to claim 1, wherein $R^1$ is an alkali metal, and $n$ is 1.

4. The composition according to claim 3, wherein $R^1$ is potassium or sodium.

5. The composition according to claim 1, wherein $R^1$ is an alkaline earth metal, and $n$ is 2.

6. The composition according to claim 5, wherein $R^1$ is calcium, zinc or magnesium.

7. The composition according to claim 1, wherein $R^2$ is hydrogen or an alkyl group having 1 to 4 carbon atoms and $R^3$ to $R^6$ are hydrogen.

8. The composition according to claim 1, wherein both $R^2$ and $R^3$ are methyl groups and $R^4$ to $R^6$ are hydrogen.

9. The composition according to claim 2, wherein $R^2$ is hydrogen or a methyl group and $R^3$ to $R^6$ are hydrogen.

10. The composition according to claim 1, wherein $R^1$ is a mono- to tetra-hydric aliphatic alcohol moiety having 1 to 12 carbon atoms.

11. The composition according to claim 10, wherein $R^1$ is a glycerin or pentaerythritol moiety.

12. The composition according to claim 11, wherein all R's are hydrogen.

13. The composition according to claim 1, wherein $R^1$ is an ammonium group or an organic amine residue, and $n$ is 1.

14. A composition represented by the formula,

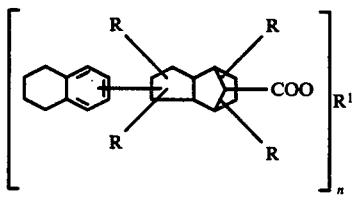

wherein R is hydrogen or an alkyl group having 1 to 3 carbon atoms, said four R groups being the same or different; $R^1$ is hydrogen, a mono- to tetra-hydric aliphatic alcohol moiety having 1 to 12 carbon atoms, an alkali or alkaline earth metal, an ammonium group, or an organic amine residue; and $n$ is an integer of 1 to 4.

15. A process for producing a composition represented by the formula,

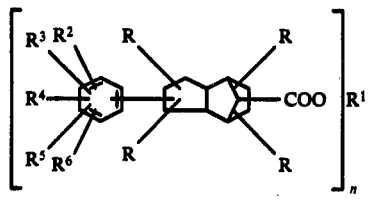

wherein R is hydrogen or an alkyl group having 1 to 3 carbon atoms, said four R groups being the same or different; $R^1$ is hydrogen, a mono- to tetra-hydric aliphatic alcohol moiety having 1 to 12 carbon atoms, an alkali or alkaline earth metal, ammonium group, or an organic amine residue; $n$ is an integer of 1 to 4; and $R^2$, $R^3$, $R^4$, $R^5$ and $R^6$, which may be the same or different, are independently hydrogen or alkyl groups having 1 to 6 carbon atoms or $R^2$ and $R^3$ may form a ring when taken together, which comprises reacting a carboxylic ester of a dimer of at least one member selected from the group consisting of cyclopentadiene and mono- to di-alkyl ($C_{1-3}$) cyclopentadienes with at least one member selected from the group consisting of benzene and benzene derivatives represented by the formula,

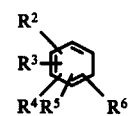

wherein $R^2$, $R^3$, $R^4$, $R^5$ and $R^6$ have the same meanings as defined above, in the presence of a Friedel-Crafts catalyst and, if necessary, hydrolyzing the resulting ester.

16. A process for producing a composition represented by the formula,

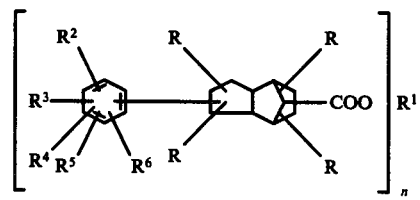

wherein $n$, R, $R^1$, $R^2$, $R^3$, $R^5$ and $R^6$ have the same meanings as defined in claim 15, which comprises reacting a nitrile of a dimer of at least one member selected from the group consisting of cyclopentadiene and mono- to di-alkyl ($C_{1-3}$)cyclopentadienes with at least one member selected from the group consisting of benzene and benzene derivatives represented by the formula,

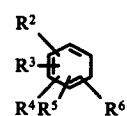

wherein $R^2$, $R^3$, $R^4$, $R^5$ and $R^6$ have the same meanings as defined in claim 15, in the presence of a Friedel-Crafts catalyst, hydrolyzing the reaction product, and, if necessary, esterifying the hydrolyzate.

17. A process for producing a composition represented by the formula,

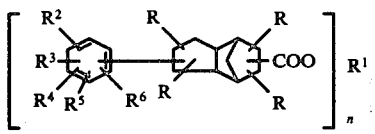

wherein $n$, R, $R^1$, $R^2$, $R^3$, $R^4$, $R^5$ and $R^6$ have the same meanings as defined in claim 15, which comprises reacting an aldehyde of a dimer of at least one member selected from the group consisting of cyclopentadiene and mono- to di-alkyl ($C_{1-3}$)cyclopentadienes with at least one member selected from the group consisting of benzene and benzene derivatives represented by the formula,

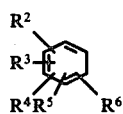

wherein $R^2$, $R^3$, $R^4$, $R^5$ and $R^6$ have the same meanings as defined in claim 15, in the presence of a Friedel-Crafts catalyst, oxidizing the reaction product, and, if necessary, neutralizing or esterifying the oxidation product.

18. The process according to claim 15, wherein the Friedel-crafts catalyst is a boron tri-fluoride compound, hydrogen fluoride, aluminum chloride, or sulfuric acid.

19. The process according to claim 18 wherein the reaction is performed at 0° to 100° C for 1 to 20 hours with stirring.

20. The process according to claim 15, wherein the hydrolyzation is effected at a temperature of 80° to 200° C in the presence of an acid or a base.

21. The process according to claim 17, wherein the oxidization is effected with chromic acid, a permanganate or silver oxide at a temperature of 0° to 80° C.

22. The process according to claim 16, wherein the esterification is effected with a mono- to tetrahydric aliphatic alcohol at a temperature of 50° to 100° C.

23. The process according to claim 15, wherein the resulting ester is subjected to transesterification at a temperature of 50° to 100° C.

24. The process according to claim 15, wherein the carboxylic ester is reacted with benzene, toluene, ethylbenzene, cumene, butylbenzene, cymene, xylene, 1,2,4-trimethylbenzene, or tetrahydroanaphthalene.

25. The process according to claim 16, wherein the nitrile is reacted with benzene, toluene, ethylbenzene, cumene, butylbenzene, cymene, xylene, 1,2,4-trimethylbenzene or tetrahydronaphthalene.

26. The process according to claim 17, wherein the aldehyde is reacted with benzene, toluene, ethylbenzene, cumene, butylbenzene, cymene, xylene, 1,2,4-trimethylbenzene or tetrahydronaphthalene.

27. A synthetic emulsifier comprising as the essential active component a composition represented by the formula,

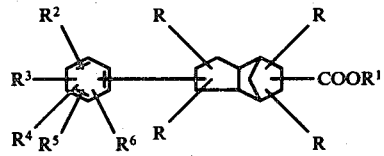

wherein R is hydrogen or an alkyl group having 1 to 3 carbon atoms, said four R groups being the same or different; $R^1$ is an alkali metal, ammonium group, or an organic amine residue; and $R^2$, $R^3$, $R^4$, $R^5$ and $R^6$ which may be the same or different, are independently hydrogen or alkyl groups having 1 to 6 carbon atoms, or $R^2$ and $R^3$ may form a ring when taken together.

28. The emulsifier according to claim 27, wherein $R^1$ is potassium, sodium, or ammonium.

29. The emulsifier according to claim 27, wherein $R^2$ is hydrogen, methyl or ethyl, $R^3$ is hydrogen, or methyl and $R^4$ to $R^6$ are hydrogen.

30. The emulsifier according to claim 29, wherein all R groups are hydrogen.

31. A sizing agent comprising as the essential active component a composition represented by the formula,

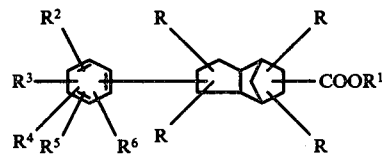

wherein R is hydrogen or an alkyl group having 1 to 3 carbon atoms, said four R groups being the same or different; $R^1$ is an alkali metal or an ammonium group; and $R^2$, $R^3$, $R^4$, $R^5$ and $R^6$, which may be the same or different, are independently hydrogen or alkyl groups having 1 to 6 carbon atoms, or $R^2$ and $R^3$ may form a ring when taken together.

32. The sizing agent according to claim 31, all R groups are hydrogen; $R^2$ is an alkyl group having 1 to 6 carbon atoms, $R^3$ and $R^4$ are hydrogen or methyl; and $R^5$ and $R^6$ are hydrogen.

33. The sizing agent according to claim 32, wherein $R^1$ is potassium or sodium.

34. An adhesive, tackifier, printing ink vehicle, or surface coating vehicle which comprises a composition represented by the formula,

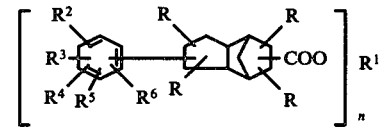

wherein R is hydrogen or an alkyl group having 1 to 3 carbon atoms, said four R groups being the same or different; $R^1$ is hydrogen, an alkali or alkaline earth metal, an ammonium group, a mono- to tetra-hydric aliphatic alcohol moiety having 1 to 12 carbon atoms, or an organic amine residue; $n$ is an integer of 1 to 4; $R^2$, $R^3$, $R^4$, $R^5$ and $R^6$, which may be the same or different, are independently hydrogen or alkyl groups having 1 to 6 carbon atoms, or $R^2$ and $R^3$ may form a ring when taken together.

* * * * *